United States Patent [19]

Palti

[11] Patent Number: 5,697,942
[45] Date of Patent: Dec. 16, 1997

[54] INTERNAL VASCULAR CLAMP

[76] Inventor: Yoram Palti, 51 Ruth St., Haifa, Israel, 34404

[21] Appl. No.: 749,487

[22] Filed: Nov. 15, 1996

Related U.S. Application Data

[63] Continuation-in-part of Ser. No. 509,203, Jul. 31, 1995, Pat. No. 5,624,454.

[30] Foreign Application Priority Data

Jul. 31, 1994 [IL] Israel ........................................ 110517

[51] Int. Cl.$^6$ ........................................ A61B 17/04
[52] U.S. Cl. ........................... 606/151; 606/157; 606/192
[58] Field of Search ........................... 606/151, 153, 606/207, 157, 158, 142, 143

[56] References Cited

U.S. PATENT DOCUMENTS

| | | |
|---|---|---|
| 3,258,012 | 6/1966 | Nakayama et al. . |
| 3,265,069 | 8/1966 | Healey et al. . |
| 3,503,398 | 3/1970 | Fogarty et al. . |
| 4,531,519 | 7/1985 | Dunn et al. . |
| 5,152,770 | 10/1992 | Bengmark et al. . |
| 5,236,437 | 8/1993 | Wilk et al. . |
| 5,282,812 | 2/1994 | Suarez, Jr. . |
| 5,391,181 | 2/1995 | Johnson et al. . |

FOREIGN PATENT DOCUMENTS

| | | |
|---|---|---|
| 1103119 | 6/1981 | Canada . |
| 214727 | 10/1909 | Germany . |

*Primary Examiner*—Gary Jackson
*Attorney, Agent, or Firm*—David M. Klein; Bryan Cave LLP

[57] ABSTRACT

A vascular clamp for occluding a blood vessel or duct during surgery, comprising a clamping element adapted to be substantially entirely positioned within a body cavity during the surgery and to avoid either mechanical or visual interference with the surgeon's operating field. The clamp comprises a pair of clamping jaws movable between a first, open position and a second, closed position, and means integral with and securing the clamping jaws to one another for movement from their open to their closed position, the securing means together with the clamping jaws defining a substantially closed internal chamber having substantially continuous internal walls when the clamping jaws are in their closed position. A balloon is mounted to the internal walls of each clamping jaw and pre-filled with a fluid under a predetermined pressure such that the balloons may completely surround and occlude the blood vessel or duct when the clamping jaws are in their closed position. Further, locking means are provided on the clamping jaws for releasably holding the clamping jaws in their closed position.

11 Claims, 5 Drawing Sheets

FIG. IA
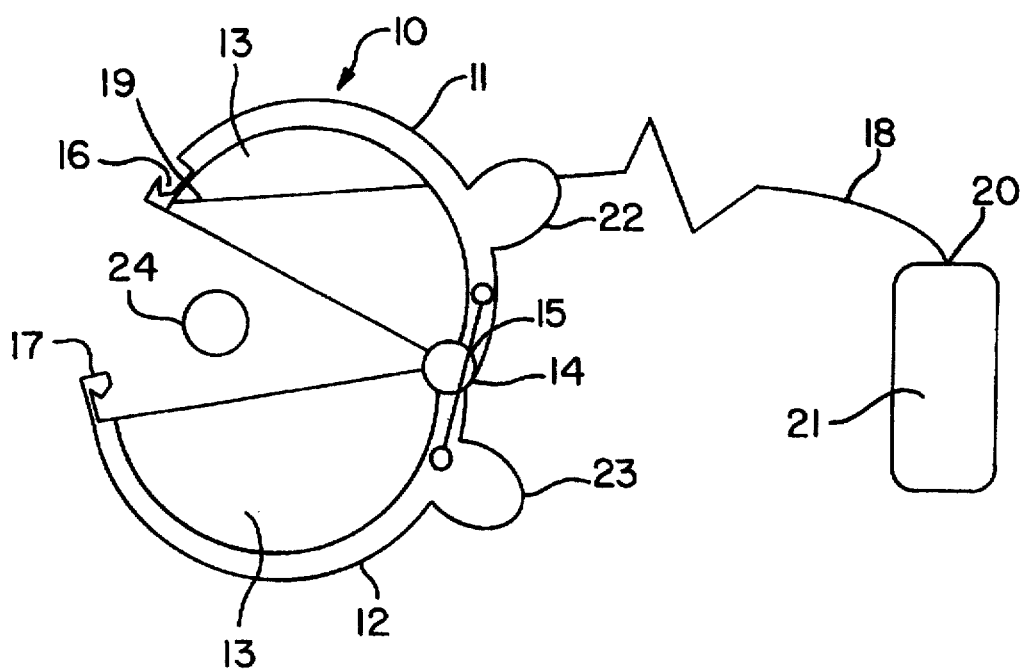
FIG. IB
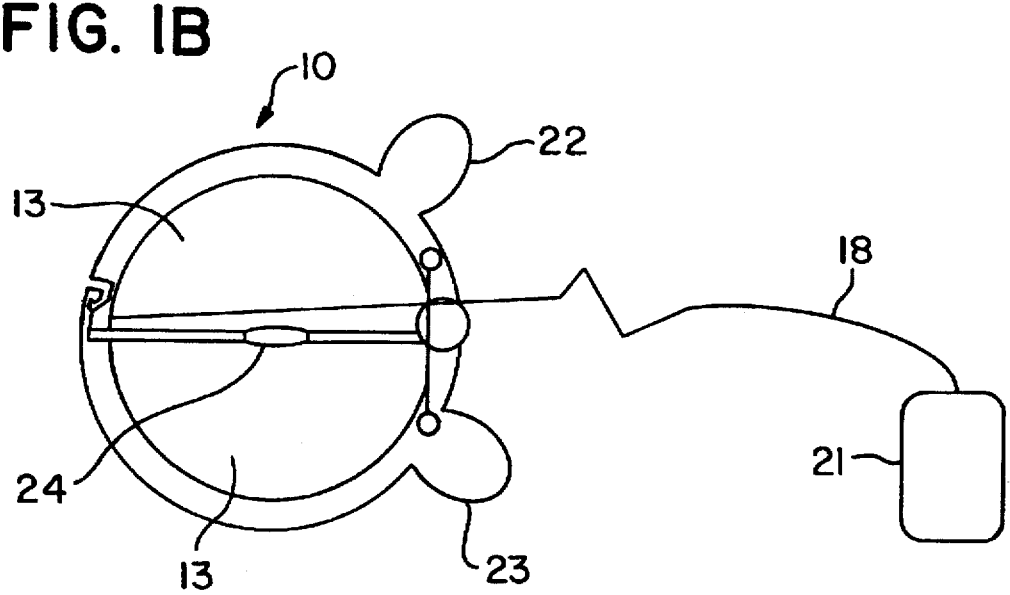

5,697,942

INTERNAL VASCULAR CLAMP

This application is a continuation-in-part of U.S. patent application Ser. No. 08/509,203, filed Jul. 31, 1995 U.S. Pat. No. 5,624,454.

The invention relates to a vascular clamp, particularly to a vascular clamp designed to be substantially entirely positioned within a body cavity during surgery and to completely occlude a blood vessel or duct without causing injury thereto during surgery, and without interfering with the operating field.

BACKGROUND OF THE INVENTION

Vascular clamps play a vital and obvious role during surgery, their task being to completely occlude a blood vessel. Conventional clamps, such as the Fogarty Clamp, the De Bakey "Atravgrip", the Bulldog Clamp, and Pott's and Satinsky's Peripheral Vascular Clamps, generate loci of extremely high pressure far in excess of the pressure in the blood vessel itself. These high pressures are apt to cause permanent injury to the blood vessel.

The clamp described in the above-identified parent application, U.S. patent application Ser. No. 08/509,203, blocks blood flow while avoiding loci of excessive pressure by surrounding the blood vessel with a uniform external pressure field generated by a pair of semicircular, fluid-filled balloons. However, the external arms of such clamp can interfere with the surgeon's view, or with the access of other instruments to a limited operating field, which may be delimited by a relatively small incision.

It is an object of the present invention to provide an internally positionable, removable vascular clamp that does not injure the blood vessel or duct to be occluded, and that may be substantially entirely positioned within the body cavity in which surgery is carried out without mechanically or visually interfering with the operating field.

Other objects and advantages of the invention will be apparent from the following description of preferred embodiments thereof.

SUMMARY OF THE INVENTION

In accordance with the present invention a vascular clamp for occluding a blood vessel or anatomical duct is provided, which comprises a clamping element adapted to be substantially entirely positioned within a body cavity in which surgery is to be performed. The clamping element includes a pair of clamping jaws movable between a first, open position and a second, closed position, and means integral with and securing the clamping jaws to one another for movement from their open to their closed position, the securing means together with the clamping jaws defining a substantially closed internal chamber having substantially continuous internal walls when the clamping jaws are in their closed position. A balloon is mounted to the internal walls of each clamping jaw and pre-filled with a fluid under a predetermined pressure such that the balloons may completely surround and occlude the blood vessel or duct when the clamping jaws are in their closed position. The elasticity of the balloons is correlated with the compressibility of the fluid charged thereto so that the pressure exerted by the balloons on the blood vessel or duct is not so large as to permanently damage the same. Finally, locking means are provided on the clamping jaws for releasably holding the clamping jaws in the closed position.

The vascular clamp thus provided exhibits the several advantages of the padded vascular clamp described in the aforesaid copending application, viz., it is able to occlude a blood vessel or anatomical duct in a patient without damaging the blood vessel or duct by exerting a predetermined and adjustable uniform circumferential pressure field thereon. Moreover, by providing the securing means integral with the clamping jaws and mounting the locking means on the clamping jaws, a self-contained, discrete and compact clamp is achieved which may be substantially entirely positioned within a body cavity about the blood vessel or duct during surgery. The vascular clamp of the invention thus does not incorporate forceps-like arms for manipulating and securing the clamp to the blood vessel or duct, which arms may extend into the operating field and both mechanically and visually interfere with the surgeon's manipulations.

In accordance with an additional feature of the invention, handle means are provided integral with the outside walls of the clamping jaws, facilitating both application of the vascular clamp to the blood vessel or duct, and release and removal of the clamp from the blood vessel or duct and from the operating field. Such handle means facilitates insertion and removal of the clamp either manually by the surgeon or with the temporary use of a forceps which may thereafter be removed to facilitate subsequent unrestricted access to the operating field.

Further, means are provided for opening the clamping jaws by releasing the locking means, permitting facile removal of the clamp from the blood vessel or duct. The opening means may, for example, be a filament attached at one end to at least one of the clamping jaws adjacent to the locking means and at its opposite end to tab means outside of the clamping element, manipulation of the tab disengaging the locking means to open the clamping jaws and permit facile removal of the clamp from the blood vessel or duct.

The invention will be further understood with reference to the following description of various preferred embodiments thereof, taken in conjunction with the annexed drawings, in which:

BRIEF DESCRIPTION OF THE DRAWINGS

FIG. 1A is a schematic, cross sectional view of one embodiment of the vascular clamp of the invention incorporating a hinge element securing the clamping jaws to one another and a handle means integral with the clamping element on the outside walls thereof, with the clamping jaws shown in their open position around a blood vessel to be occluded therewith;

FIG. 1B is a schematic, cross-sectional view of the embodiment of FIG. 1A, with the clamping jaws shown in their closed position, occluding the blood vessel;

DESCRIPTION OF THE PREFERRED EMBODIMENTS

Figure 2A:
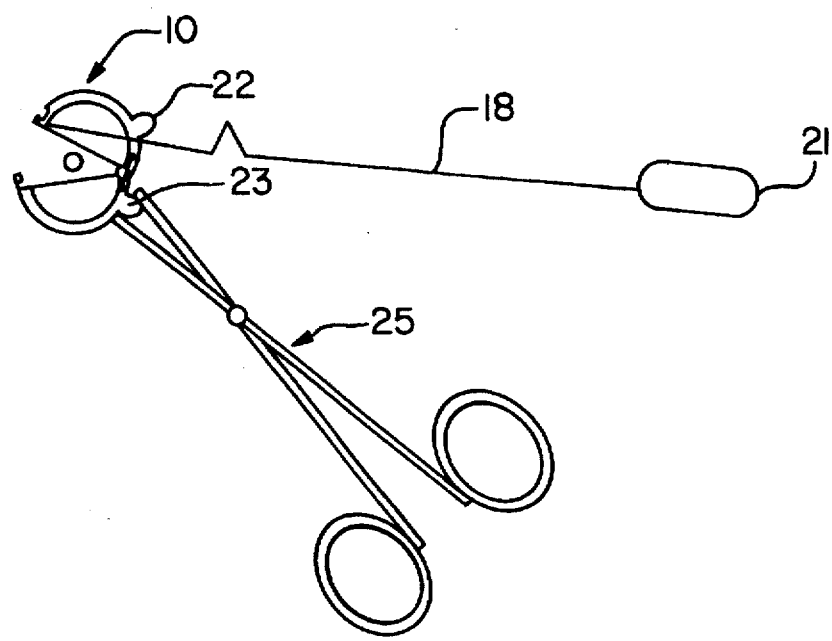
FIG. 2A is a schematic, cross sectional view illustrating the manner of applying the clamp of FIG. 1A around a blood vessel or duct with a forceps, during surgery.

Referring initially to FIGS. 1A, 1B, 2A and 2B, a first embodiment of the vascular clamp of the invention, generally indicated at 10, includes a pair of clamping jaws 11 and 12 having substantially semi-cylindrical shapes. A fluid-filled balloon 13 is mounted to the internal walls of each clamping jaw. The jaws 11 and 12 may be made of stainless steel, a biocompatible plastic or some other inert material, and the balloons may be made of rubber or other elastomeric material, tightly mounted to the internal walls of the clamping jaws and filled with air, water or other inert fluid to any predetermined pressure, all as more fully described in the aforesaid copending application the disclosure of which is incorporated by this reference herein.

The clamping jaws are connected to one another by a hinge 14 including a spring 15 normally biasing the clamping jaws into a first, open position as shown in FIG. 1A. A locking means comprising a notch 16 and a detent 17 is formed in the adjacent outer walls of clamping jaws 11 and 12, respectively, to facilitate locking the clamping jaws into the second, closed position shown in FIG. 1B. A filament 18, e.g., a nylon or Teflon® thread or stainless steel wire, is secured at one end 19 to the inside wall of clamping jaw 11, threaded through an aperture in the clamp 10 (not shown) and secured at its opposite end 20 to a release tab 21. The release tab may extend outwardly of the body during surgery to locate the clamp 10, and is used to release the clamping jaws 11 and 12 after the surgery, as described below. Handle means comprising knobs 22 and 23 formed on opposite sides of hinge 14 on the external surfaces of the clamping jaws, are additionally provided on the clamp to facilitate gripping the clamping element for application to and removal from a blood vessel or duct, indicated at 24, during the surgery.

Figure 2B:
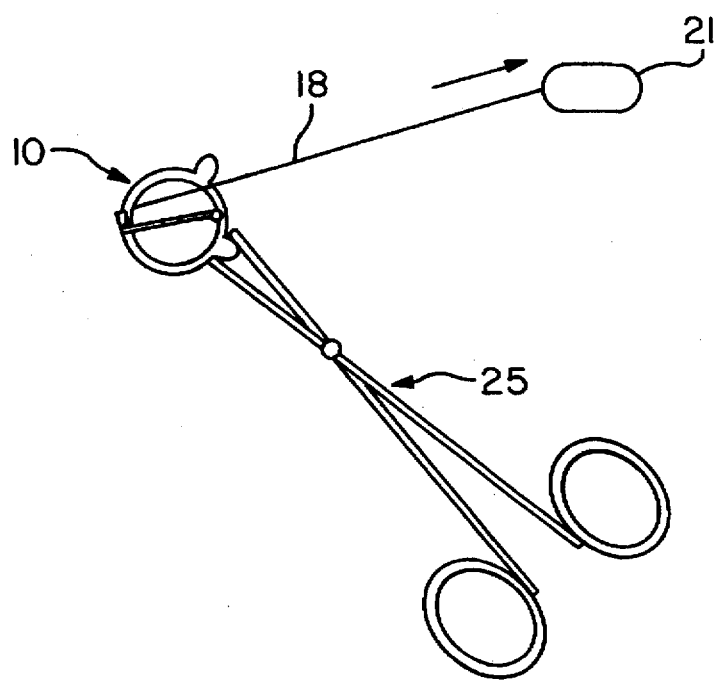
FIG. 2B is a schematic, cross sectional view illustrating the manner of releasing the clamp of FIG. 1B from around a blood vessel or duct with a forceps after surgery.

As shown in FIGS. 2A and 2B, the clamp 10 may be applied to the blood vessel or duct 24 by gripping either (or both) of knobs 22 and 23 with a surgical forceps 25. The surgeon thus manipulates the clamp into the position shown in FIG. 2A, with the jaws 11 and 12 biased by spring 15 into their open position around the blood vessel or duct. When it is desired to close the clamp to occlude the blood vessel or duct 24 (as shown in FIG. 1B) the surgeon may manually apply pressure to the outer surfaces of jaws 11 and 12, thereby overcoming the force of spring 15, until the pressure of the balloons 13 occludes the blood vessel or duct and the detent 16 and notch 17 of the locking mechanism engage, thus securing the clamping jaws in their closed position during the surgery. Upon completion of the surgery or whenever the surgeon is ready to remove the clamp from the blood vessel or duct, he pulls release tab 21 whereby filament 18 disengages the detent 17 from the notch 16 of the locking mechanism, the clamping jaws 11 and 12 being forced into the open position (FIG. 1A) by the biasing spring 15 to release the clamp from the blood vessel or duct. The clamp may then be removed from the operating field by grasping knob 23 with the forceps 25 and withdrawing the same.

Figure 3A:
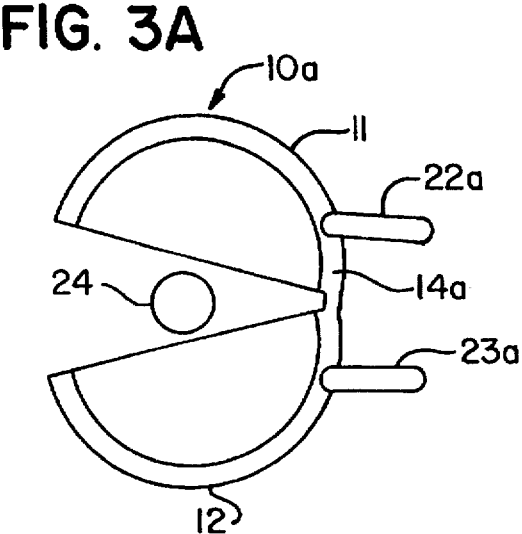
FIG. 3A is a schematic, cross sectional view of a further embodiment of the vascular clamp, with a different form of handle means and incorporating a flexible element securing the clamping jaws to one another, with the clamping jaws shown in their open position around a blood vessel to be occluded therewith.
Figure 3B:
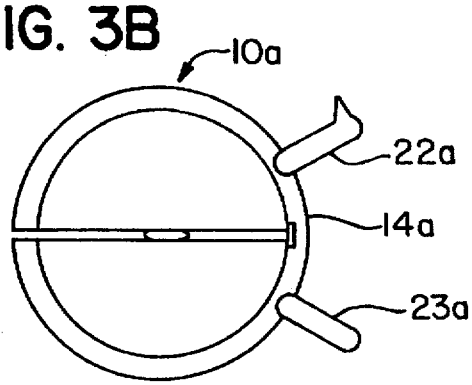
FIG. 3B is a schematic, cross sectional view of the embodiment of FIG. 3A, with the clamping jaws shown in their closed position, occluding the blood vessel.

Another embodiment 10a of the clamp of the invention is shown in FIGS. 3A and 3B. In this embodiment, in lieu of the hinge 14 the clamping jaws 11 and 12 are connected to one another by a relatively thin, elastic member 14a which is normally biased toward the closed position of the clamping jaws. The handle elements 22a and 23a are elongated ribs, making it easier to pinch them toward one another, thus opening the clamp as shown in FIG. 3A. When the handle elements are released, the clamp 10a closes, occluding the blood vessel as shown in FIG. 3B.

Figure 4A:
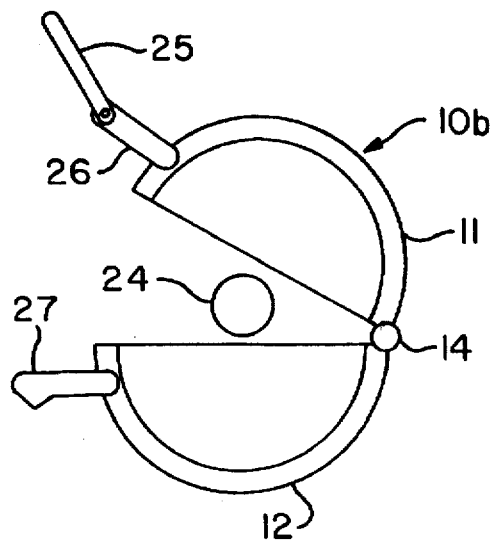
FIG. 4A is a schematic, cross sectional view of yet a further embodiment of the vascular clamp, incorporating a hinge securing the clamping jaws to one another, a form of locking element distinct from that in the embodiment of FIG. 1 and without an independent handle means integral with the clamping element, with the clamping jaws shown in their open position around a blood vessel to be occluded therewith.
Figure 4B:
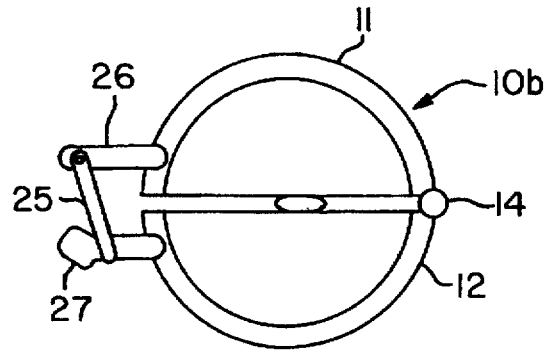
FIG. 4B is a schematic, cross sectional view of the embodiment of FIG. 4A, with the clamping jaws shown in their closed position, occluding the blood vessel.

In the embodiment 10b of the invention shown in FIGS. 4A and 4B, the two clamping jaws 11 and 12 are connected by hinge 14, which permits the clamping jaws to pivot between their open position shown in FIG. 4A and their closed position shown in FIG. 4B. In this embodiment, a locking means is provided comprising a latch member 25 pivoted to a first support 26 and engageable with a shouldered, second support 27.

Upon manual closure of the clamping jaws 11 and 12, the latch 25 may be pivoted over the shoulder of support 27, holding the clamp 10b in the closed position shown in FIG. 4B with the blood vessel or organ occluded. By a slight further squeeze of the clamping jaws (or the supports 26 and 27 of the latching mechanism) the latch member 25 may be disengaged, permitting the spring-loaded hinge 14 to return the clamping jaws to their open position (FIG. 4A).

Figure 5:
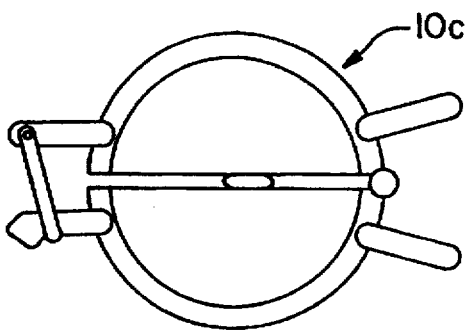
FIG. 5 is a schematic, cross sectional view of another embodiment, similar to that shown in FIGS. 4A and 4B but incorporating a handle means similar to that incorporated in the embodiment of FIGS. 3A and 3B.

The embodiment 10c of the clamp of the invention shown in FIG. 5 combines the elongated handle elements 22a and 23a of clamp 10a (FIGS. 3A and 3B) with the latching mechanism illustrated in FIGS. 4A and 4B.

Figure 6:
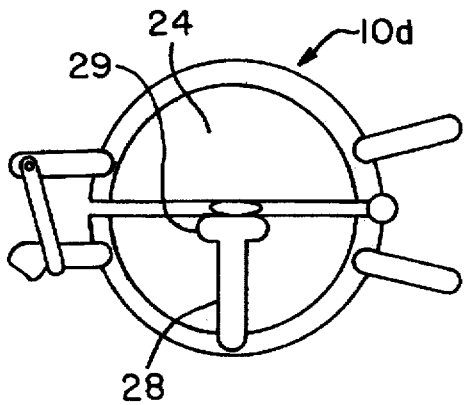
FIG. 6 is a schematic, side elevation of another embodiment, similar to that shown in FIG. 5 but incorporating an external support for the blood vessel or duct to facilitate the insertion of a catheter.
Figure 7:
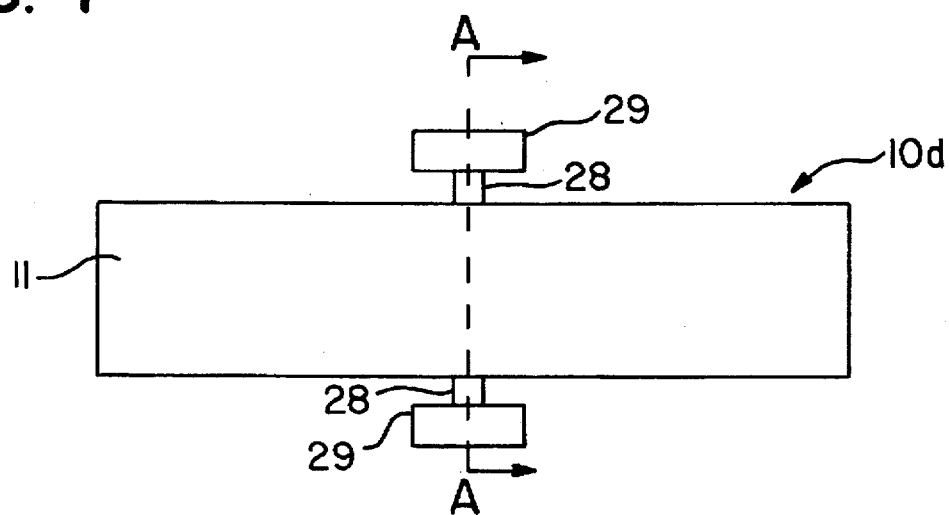
FIG. 7 is a schematic, top plan view of the embodiment of FIG. 6.
Figure 8:
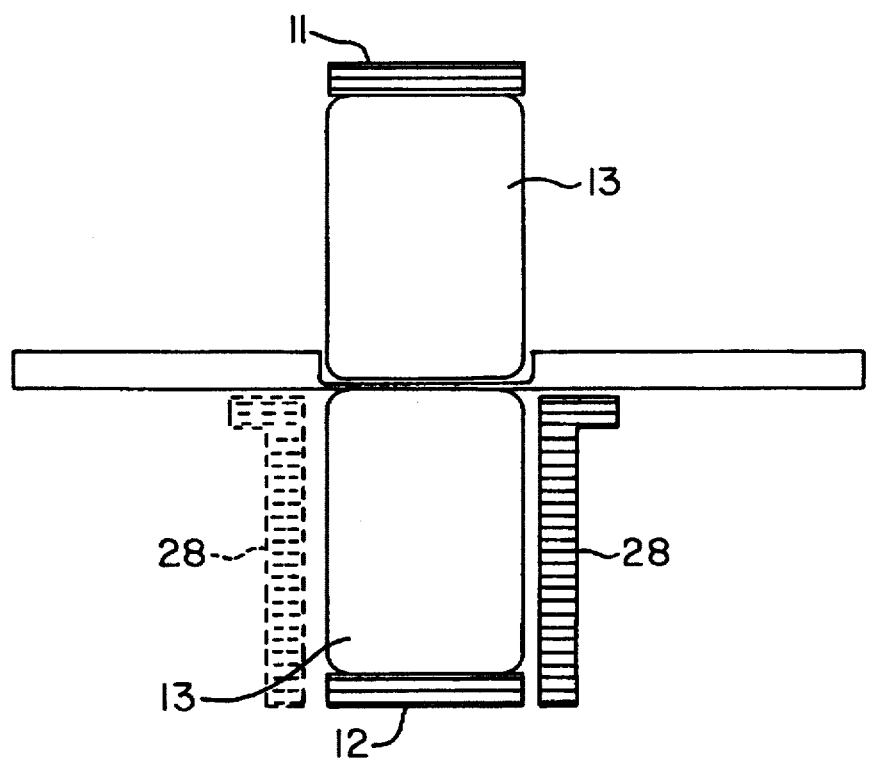
FIG. 8 is a schematic, cross section view of the embodiment of FIGS. 6 and 7, viewed in the direction of line A—A in FIG. 7.

In yet a further embodiment 10d of the clamp shown in FIGS. 6–8, support members 28 are mounted on the clamp externally of the clamping jaw 12 outside the balloon 13 secured thereto. The support members terminate in flanges 29 for alignment with and support of the blood vessel or duct 24 to facilitate the insertion of a catheter therein. If desired, only one such support member 28 may be provided.

Figure 9:
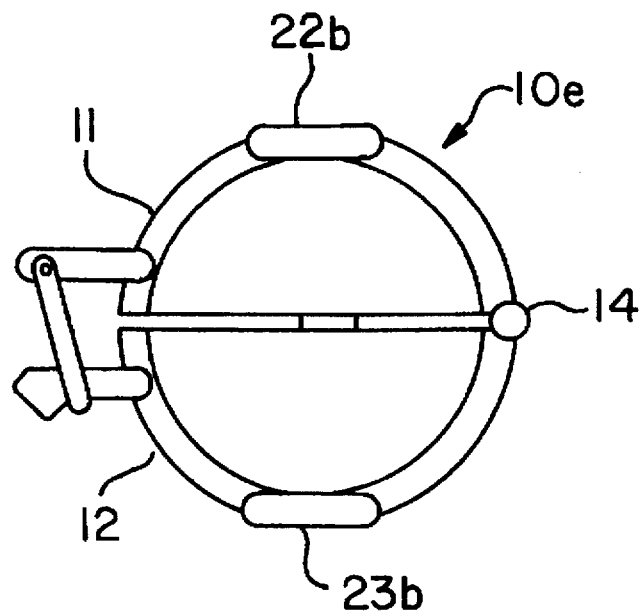
FIG. 9 is a schematic, cross sectional view of another embodiment, similar to that shown in FIG. 5 but incorporating a different form of handle means.
Figure 10:
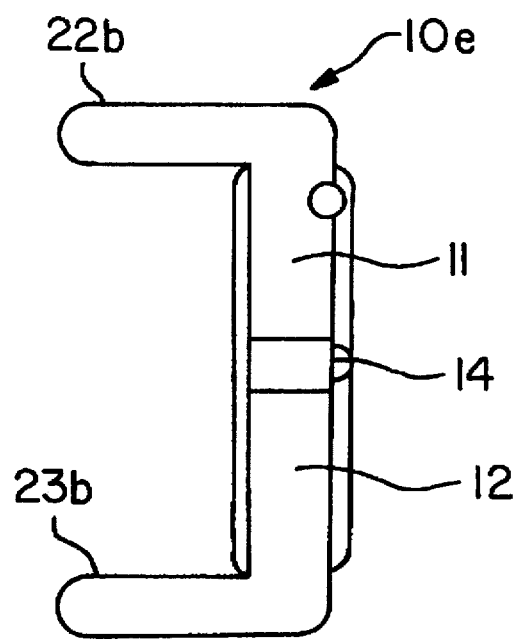
FIG. 10 is a schematic, side elevation of the embodiment of FIG. 9.

FIGS. 9 and 10 illustrate yet another embodiment of the invention, in which handle elements 22b and 23b are provided, integral with clamping jaws 11 and 12 but extending in planes essentially perpendicular to the planes in which clamping jaws 11 and 12 lie, allowing the surgeon to manipulate the clamp 10e from one end thereof.

It will be understood that further variations of the preferred embodiments of the vascular clamp described hereinabove may be made without departing from the scope of the present invention. Accordingly, it is intended that the invention embraces such other modifications as are within the scope of the claims appended hereto.

I claim:

1. A vascular clamp for occluding a blood vessel or duct, comprising a clamping element adapted to be substantially entirely positioned within a body cavity about the blood vessel or duct, and including:

(a) a pair of clamping jaws movable between a first, open position and a second, closed position;

(b) means integral with and securing the clamping jaws to one another for movement from their open to their closed position, the securing means together with the clamping jaws defining a substantially closed internal chamber having substantially continuous internal walls when the clamping jaws are in the closed position;

(c) a balloon mounted to the internal walls of each clamping jaw and pre-filled with a fluid under a predetermined pressure such that the balloons completely surround and occlude the blood vessel or duct in the closed position of the clamping jaws; and (d) locking means on the clamping jaws for releasably holding the clamping jaws in the closed position.

2. The clamp of claim 1, in which the clamping jaws are substantially semi-cylindrical and in which the securing means together with the clamping jaws, define a substantially cylindrical internal chamber when the clamping jaws are in the closed position.

3. The clamp of claim 1, further comprising handle means integral with the clamping element on the outside walls thereof, for applying the vascular clamp to the blood vessel or duct and releasing and removing the vascular clamp therefrom.

4. The clamp of claim 1, further comprising means for opening the clamping jaws by releasing the locking means to permit removal of the clamp from the blood vessel or duct.

5. The clamp of claim 4, wherein the means for opening the clamping jaws comprises a filament secured at one end to at least one of the clamping jaws adjacent the locking means, and tab means at its opposite end outside the clamping element.

6. The clamp of claim 1, wherein the securing means is a spring-biased hinge normally biasing the clamping jaws into their open position.

7. The clamp of claim 1, wherein the securing means is a flexible wall element integral with the clamping jaws and permitting movement of the clamping jaws between their open and closed positions.

8. A vascular clamp for occluding a blood vessel or duct, comprising a clamping element adapted to be substantially entirely positioned within a body cavity about the blood vessel or duct, and including:

(a) a pair of substantially-semicylindrical clamping jaws movable between a first, open position and a second, closed position;

(b) means integral with and securing the clamping jaws to one another for movement from their open to their closed position, the securing means together with the clamping jaws defining a substantially cylindrical closed internal chamber having substantially continuous internal walls when the clamping jaws are in the closed position;

(c) a balloon mounted to the internal walls of each clamping jaw and pre-filled with a fluid under a predetermined pressure such that the balloons completely surround and occlude the blood vessel or duct in the closed position of the clamping jaws;

(d) handle means integral with the clamping element on the outside walls thereof, facilitating application of the vascular clamp to the blood vessel or duct and release and removal of the vascular clamp therefrom; and (e) locking means on the clamping jaws for releasably holding the clamping jaws in their closed position.

9. The clamp of claim 8, further comprising means for opening the clamping jaws by releasing the locking means to permit removal of the clamp from the blood vessel or duct.

10. The clamp of claim 9, wherein the means for opening the clamping jaws comprises a filament secured at one end to at least one of the clamping jaws adjacent the locking means, and at its opposite end to tab means outside the clamping element.

11. The clamp of claim 8, wherein the securing means is a spring-biased hinge normally biasing the clamping jaws into their open position.

* * * * *